United States Patent [19]

Grodberg

[11] Patent Number: 5,153,005

[45] Date of Patent: Oct. 6, 1992

[54] COMPOSITION AND METHOD FOR PREVENTING FLUOROSIS

[75] Inventor: Marcus G. Grodberg, Newton, Mass.

[73] Assignee: Colgate-Palmolive Company, Piscataway, N.J.

[21] Appl. No.: 625,563

[22] Filed: Dec. 11, 1990

[51] Int. Cl.⁵ .................... A61K 7/18; A61K 33/16
[52] U.S. Cl. ............................ 424/676; 424/52; 424/673; 426/74
[58] Field of Search ............... 424/52, 606, 673, 676

[56] References Cited

U.S. PATENT DOCUMENTS

| | | | |
|---|---|---|---|
| 4,083,955 | 4/1978 | Grabenstetter et al. | 424/52 |
| 4,169,885 | 10/1979 | Raaf et al. | 424/676 |
| 4,397,837 | 8/1983 | Raaf et al. | 424/676 |
| 4,424,203 | 1/1984 | Pakhomov et al. | 424/676 |
| 4,460,565 | 7/1984 | Westrate et al. | 424/52 |
| 4,556,561 | 12/1985 | Brown et al. | 424/52 |
| 4,627,978 | 12/1986 | Lynch | 424/49 |
| 4,693,888 | 9/1987 | Miyahara et al. | 424/52 |
| 4,726,952 | 2/1988 | Walsdorf et al. | 424/676 |
| 4,728,513 | 3/1988 | Ventouras | 424/676 |
| 4,784,858 | 11/1988 | Ventouras | 424/468 |
| 4,859,467 | 8/1989 | Grodberg et al. | 424/676 |
| 4,861,590 | 8/1989 | Grodberg | 424/606 |
| 4,904,478 | 2/1990 | Walsdorf et al. | 424/468 |
| 4,915,948 | 4/1990 | Gallopo et al. | 424/49 |
| 5,013,728 | 5/1991 | Grodberg | 424/676 |

FOREIGN PATENT DOCUMENTS

| | | | |
|---|---|---|---|
| 731578 | 6/1969 | Belgium | 424/676 |
| 1237082 | 5/1988 | Canada | 424/676 |
| 1013756 | 8/1952 | France | 424/676 |
| 2239205 | 2/1975 | France | 424/676 |
| 1221633 | 2/1971 | United Kingdom | 424/676 |
| 1249852 | 10/1971 | United Kingdom | 424/676 |

OTHER PUBLICATIONS

Ericsson C.A. 73:38547d (1970) of Belg. 731,578.
Ruzicka et al C.A. 82:1188799 (1974).
Fuchs et al C.A. 91:186370c (1979).
Biotherapie C.A. 83:183398s (1985) of Fr. Dem. 2,239,205.
Skobe et al C.A. 103:135128p (1985).
Villa et al C.A. 110:2304885 (1989).
Trautner et al C.A. 110:128095s (1989).
Trautner et al C.A. 111:83977h (1989).

*Primary Examiner*—Shep K. Rose
*Attorney, Agent, or Firm*—Paul Shapiro; Robert C. Sullivan

[57] ABSTRACT

A fluorosis-free ingestible fluoride ion-containing composition comprising a mixture of pharmaceutically acceptable fluoride and monofluorophosphate in a weight ratio to provide not more than about fifty percent, and preferably not more than about twenty-five percent, of available fluoride ion from the fluoride and the balance from the monofluorophosphate. By "fluorosis-free" composition is meant one which, when ingested, minimizes or obviates the occurrence of fluorosis which is a common effect when fluoride is ingested. The composition may contain additional pharmaceutically acceptable adjuvants, such as vitamins, coloring, flavoring, carriers, stabilizers, preservatives, medicants and the like, and may be in the form of a powder, tablet, capsule, pill or a liquid in a suitable ingestible carrier. Preferred compounds are alkali metal, ammonium and amine fluorides and monofluorophosphates. Most preferred compounds are sodium fluoride (NaF) and sodium monofluorophosphate (MFP), whose formula is $Na_2FPO_3$ and the corresponding potassium salts.

The compositions are especially adapted for use as a dietary supplement to provide substantially instantaneous low-dosage fluoride ion from the fluoride compound upon ingestion and a slow, prolonged release of fluoride ion from the monofluorophosphate.

9 Claims, No Drawings

COMPOSITION AND METHOD FOR PREVENTING FLUOROSIS

BACKGROUND OF THE INVENTION

1. Field of the Invention

This invention relates to a fluorosis-free ingestible fluoride ion-containing composition useful as a dietary supplement for use alone or as an additive to milk, baby formula or other beverages or foods for users of all ages, particularly infants and young children.

2. Description of the Prior Art

In U.S. Pat. Nos. 4,859,467 and 4,861,590 there are disclosed a fluoride ion-containing compositions which provide a slow release combination to avoid gastrointestinal discomfiture from the release of fluoride ion. These patents disclose the use of monofluorophosphate (MFP) with or without the addition of sodium fluoride (NaF) and in conjunction with calcium. These slow release formulations are especially designed for adult use in treating osteoporosis.

Daily dietary supplements of sodium fluoride have been found to be effective in preventing dental decay, but have produced cosmetically objectionable fluorosis (mottling) on anterior upper incisor teeth as set forth in "Effects of Fluoride Supplementation from Birth on Human Deciduous and Permanent Teeth," Aasenden, Roland Peebles, TC, Arch Oral Biol 19, 1974. As a result, in 1979, The American Dental Association and the American Academy of Pediatrics recommended a fifty percent reduction in the daily dose for children under two years old. The new dosage established at that time became 0.25 mg fluoride ion (from 0.55 mg sodium fluoride). As a result, the dosage age schedule is more closely related to changes in body weight during infancy and childhood. See American Academy of Pediatrics, Committee on Nutrition: Fluoride supplementation, "Revised Dosage Schedule," Pediatrics 63, 1979.

However, there is still concern about the rate of fluoride dosing because animal studies have shown that "peak" blood fluoride levels, above the therapeutic range, can produce fluorosis. Therefore, in order to avoid peak levels, it is desirable to modify the conventional once a day dosing into divided doses, as occurs naturally with fluoridated drinking water. Alternatively, the use of a slow-release composition once daily is more convenient to administer as set forth in U.S. Pat. Nos. 4,859,467 and 4,861,590. However, the latter relate to compositions especially adapted for adults for use in ameliorating osteoporosis and are not specific with regard to mixtures of sodium monofluorophosphate and sodium fluoride which provide fluorosis-free advantage upon ingestion.

The fluorosis-free composition of the present invention is distinct from non-ingested oral treatment compositions containing binary fluoride sources of sodium fluoride and sodium monofluorophosphate such as are described in U.S. Pat. Nos. 4,152,419, 4,425,324 and 4,528,181, as well as British Patent No. 1 435 624.

DESCRIPTION OF THE INVENTION

In accordance with the present invention, for infants and children it has been found that a combination of a pharmaceutically acceptable fluoride such as sodium fluoride (NaF) and a monofluorophosphate, such as sodium monofluorophosphate (MFP) provides an ingestible composition for fluorosis-free anticaries treatment which is uniquely compatible with dietary products, and particularly calcium-containing foods, such as milk. Sodium monofluorophosphate is known to be slowly metabolized by an intestinal enzyme, alkaline phosphatase, converting monofluorophosphate into free fluoride ion which, in turn, is absorbed into the bloodstream. (See Ericsson's "Monofluorophosphate Physiology: General Considerations," Caries Research 17, 1983, Supplement 1.) By providing not more than about fifty percent, and preferably not more than about twenty-five percent, of the total fluoride as sodium fluoride, fluoride ions are immediately available for absorption from the stomach, resulting in serum levels approximating that obtained from drinking fluoridated water. This is then sustained by slow release of fluoride ion from monofluorophosphate in the intestines over an extended time period, such as about an eight-hour period.

Although enzymatic conversion of monofluorophosphate into fluoride is not normally 100%, it has been found that the administration of sodium fluoride increases alkaline phosphatase intestinal levels, thereby enhancing the formation of fluoride from monofluorophosphate.

Whereas it is known that the administration of sodium fluoride is incompatible with calcium-containing foods, like milk, because the absorption of the resulting calcium fluoride reaction product is rather limited (see Spak, Ekstrand and Zylberstein's "Bioavailability of Fluoride added to Baby Formula and Milk," Carries Research 16, 1982), this problem is overcome by use of monofluorophosphate, which forms soluble calcium monofluorophosphate. Likewise, interference by dietary trace minerals, such as magnesium and zinc, is also avoided by use of monofluorophosphate.

While the invention is applicable to the alkali metal, ammonium and amine cations, the preferred by far, is the sodium salt. In sodium fluoride, where the fluoride ion is immediately available as such, the available fluoride constitutes 45% by weight of the amount of sodium fluoride present; with sodium monofluorophosphate (MFP) the potential available fluoride constitutes 13% of the weight of the compound. Thus, the amount of fluoride ion from sodium fluoride is about three and one half times the potential amount from an equal weight of monofluorophosphate; therefore, at a weight ratio of monofluorophosphate to NaF of 3.5:1, we have about fifty percent of the total fluoride ion from NaF and fifty percent from monofluorophosphate. At a 7:1 weight ratio (MFP/NaF), we have one third of the fluoride from NaF and two thirds from MFP. Still further, at a weight ratio of MFP to NaF of about 10.5:1, we have twenty-five percent of the fluoride ion from NaF and seventy-five percent from MFP.

In general, it is desirable to maintain the ratio of monofluorophosphate to sodium fluoride so as to provide between about five to fifty percent of total fluoride ion from sodium fluoride and from about fifty to ninety-five percent of total fluoride ion from MFP; preferably ten to forty percent fluoride ion from sodium fluoride and sixty to eighty percent from MFP; more preferably fifteen to thirty-five percent fluoride ion from sodium fluoride and sixty-five to eighty-five percent from MFP and, most preferably, twenty to thirty percent fluoride ion from sodium fluoride and seventy to ninety percent from MFP. Within the latter range, twenty-five percent fluoride ion from sodium fluoride and seventy-five percent from MFP is a typically outstanding ratio.

Unlike sodium fluoride alone, monofluorophosphate (e.g. sodium MFP) and sodium fluoride combinations are compatible with vitamin-mineral pharmaceutical compositions, such as used in pre- and post-natal dietary supplements.

Ingestible drops, preferably aqueous, which can be added to milk, formula for infants, and like beverages, form an ideal vehicle for providing a desired dosage for infants and up to teenagers while aiding in the prevention of fluorosis. It is convenient to prepare such compositions so that they provide from about 0.05 to about 0.38 mg of total fluoride ion per drop, whereby a few drops can provide from about 0.25 mg fluoride which is the total recommended dosage for infants to 1.0 mg, the recommended dosage from three years of age to the teens.

The following Table I illustrates varying ratios of NaF and MFP (and the ratio of fluoride ions therefrom) useful herein:

TABLE I

| Weight Ratio of MFP/NaF | Ratio of F from MFP to NaF |
| --- | --- |
| 1.52/.11 | 4.0 |
| 1.44/.13 | 3.2 |
| 1.33/.15 | 2.6 |
| 1.71/.055 | 9.0 |
| 3.5/1.0 | 1.0 |

EXAMPLE 1

An aqueous composition is prepared combining 800 mg of MFP and 70 mg of sodium fluoride dissolved in sufficient water to make 100 ml of solution. This solution contains 1.36 mg F-/ml (1.04 mg from MFP and 0.32 from NaF). On the basis of 18 drops/ml, the composition contains 0.076 mg F-/drop.

To give a daily dose of about 0.25 mg to an infant would require about three drops from a dropper calibrated at eighteen drops/ml. Utilizing a dropper calibrated at 21 drops/ml, one would give four drops to an infant. For older children in the two to three year range, one would double the dosage (i.e. six or eight drops per day) and, above three years of age, double the dosage again.

EXAMPLE 2

To 100 ml of a convenient infant aqueous vitamin formulation containing Vitamins A, C, D, E, $B_1$, $B_2$, $B_6$, $B_{12}$ and Niacin, there are added 800 mg of MFP and 80 mg of sodium fluoride. This fluoride-augmented vitamin preparation dispenses about 0.075 mg/drop of fluoride ion (F-) from an 18 drop/ml dropper.

EXAMPLE 3

6.15 g of sodium monofluorophosphate and 0.444 g sodium fluoride are dissolved in 50 ml of water and this solution is added to 350 ml of a commercial vitamin formulation combining Vitamins A, C and D. The resultant solution contains 2.5 mg/ml of total available fluoride ion. Using a dropper designed to deliver twenty drops per ml, two drops will deliver 0.25 mg fluoride ion (total daily recommended dosage for infants) with low peak fluoride levels to minimize fluorosis.

With respect, specifically, to combinations of sodium fluoride and sodium monofluorophosphate, the aforedescribed prescriptions of fluoride salt and monofluorophosphate may further be defined in terms of percent by weight of each. Thus, one may employ from about 1.5 to about 2% by weight sodium fluoride and from about 75 to about 98.5% of sodium monofluorophosphate.

As previously described, one may utilize fluoride combinations of this invention in many forms. Exemplifications in liquid form permitting dispensing in drop form have been given.

The following illustrates the preparation of a vitamin tablet for use by children over three years of age:

The following are mixed and pressed into an ingestible tablet:

0.44 mg sodium fluoride
6.08 mg sodium monofluorophosphate
Vitamins A, C, D, E, B—Vitamins, Minerals, Calcium Carbonate and Tablet excipients The foregoing tablet is formulated to provide about one milligram of fluoride ion which is suitable for use by older children (three years and up), adults and pre-natal women.

What is claimed is:

1. An ingestible fluoride ion-containing composition providing a therapeutic dose of fluoride for anticaries benefits consisting essentially of an ingestible drop dosage mixture of a pharmaceutically acceptable fluoride salt and monofluorophosphate to provide on a weight basis from about 5% to 50% of fluoride ion from the fluoride salt and from about 50% to 95% of fluoride ion from the monofluorophosphate, the mixture providing fluorosis-free advantage upon ingestion.

2. An ingestible composition according to claim 1, wherein from about 10% to 40% of fluoride ion is from the fluoride salt and from about 60% to 90% is from the monofluorophosphate.

3. An ingestible composition according to claim 1, wherein from about 20% to 30% of fluoride ion is from the fluoride salt and from about 70% to 80% is from the monofluorophosphate.

4. An ingestible composition according to claims 1 to 3, wherein the fluoride salt is sodium or potassium fluoride and the monofluorophosphate is the sodium or potassium salt.

5. An ingestible composition according to claim 4, including water in sufficient quantity to dissolve the fluoride salt and the monofluorophosphate.

6. An ingestible fluoride ion containing dietary supplement composition providing a therapeutic dose of fluoride for anticaries benefits consisting essentially of an ingestible aqueous drop dosage solution containing a mixture of from about 1.5% to about 25% by weight of sodium or potassium fluoride and from about 75% to 98.5% by weight of sodium or potassium monofluorophosphate, the mixture providing fluorosis-free advantage upon ingestion.

7. An ingestible composition as defined in claim 4, including one or more of pharmaceutically acceptable flavoring, color, carrier, binder and preservative.

8. In a method for preventing or minimizing the mottling of teeth in children caused by fluorosis occasioned by the ingestion of therapeutic doses of fluoride for anticaries benefits, the improvement which comprises administering a unit dose of a composition as defined in claims 1 through 7.

9. In a method as defined in claim 8, wherein the unit dose composition contains from about 0.25 mg to about 1 mg of biochemically available fluoride.

* * * * *